United States Patent [19]

Goetz et al.

[11] 4,187,227
[45] Feb. 5, 1980

[54] MANUFACTURE OF 2,4-DIOXO-OXAZOLIDINES

[75] Inventors: Norbert Goetz, Worms; Dietrich Mangold, Neckargemuend; Bernd Zeeh, Ludwigshafen, all of Fed. Rep. of Germany

[73] Assignee: BASF Aktiengesellschaft, Fed. Rep. of Germany

[21] Appl. No.: 879,724

[22] Filed: Feb. 21, 1978

[30] Foreign Application Priority Data

Mar. 17, 1977 [DE] Fed. Rep. of Germany ....... 2711659

[51] Int. Cl.$^2$ ............................................. C07D 263/44
[52] U.S. Cl. ..................................... 548/226; 424/272
[58] Field of Search ..................................... 260/307 B

[56] References Cited

U.S. PATENT DOCUMENTS

| | | | |
|---|---|---|---|
| 2,476,559 | 7/1949 | Nawiasky et al. | 260/244 |
| 2,928,840 | 3/1960 | Shapiro et al. | 260/307 |

FOREIGN PATENT DOCUMENTS 2207576  8/1973  Fed. Rep. of Germany .

*Primary Examiner*—Jose Tovar
*Attorney, Agent, or Firm*—Keil & Witherspoon

[57] ABSTRACT

2,4-Dioxo-oxazolidines are manufactured by reacting aromatic amines with α-hydroxycarboxylic acid derivatives of the formula.

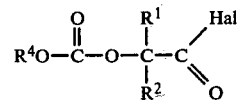

Where $R^1$ and $R^2$ have the above meanings, Hal is halogen, preferably chlorine, and $R^4$ is alkyl of 1 to 4 carbon atoms in the presence of a base, preferably at 20–120° C.

2 Claims, No Drawings

MANUFACTURE OF 2,4-DIOXO-OXAZOLIDINES

The present invention relates to a new process for the manufacture of 2,4-dioxo-oxazolidines by reacting α-hydroxy-carboxylic acid derivatives with aromatic amines.

The manufacture of 2,4-dioxo-oxazolidines from α-hydroxy-alkanecarboxylic esters and isocyanates has been disclosed (Elderfield, Heterocyclic Compounds (Wiley, New York 1957), volume 5, pages 411–417, German Published Application DAS No. 1,811,843 and German Laid-Open Application DOS No. 2,022,494). It is a disadvantage of these processes that the starting materials are isocyanates, some of which are relatively expensive products and, being rather reactive, tend to undergo changes on prolonged storage.

We have found that a 2,4-dioxo-oxazolidine of the formula I

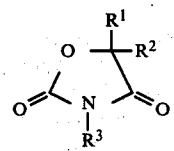

where $R^1$ and $R^2$ are identical or different and each is an aliphatic radical of 1 to 4 carbon atoms, preferably methyl or vinyl, and $R^3$ is an aromatic radical of 6 to 12 carbon atoms which may or may not be substituted by chlorine, bromine, fluorine, methyl or methoxy, preferably phenyl, is obtained in an advantageous manner if an α-hydroxy-carboxylic acid derivative of the formula II

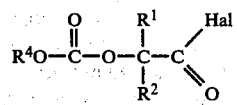

where $R^1$ and $R^2$ have the above meanings, Hal is halogen, preferably chlorine, and $R^4$ is alkyl of 1 to 4 carbon atoms, is reacted with an aromatic amine of the formula III

$$R^3-NH_2 \qquad III$$

where $R^3$ has the above meaning, in the presence of a base, preferably a tertiary amine, at from 0° to 150° C., preferably from 20° to 120° C.

The advantage of the process according to the invention is that instead of the isocyanates, which are difficult to obtain, aromatic amines, which are industrially readily obtainable and cheap, can be used as starting materials.

Examples of suitable starting materials II are 2-(methoxycarbonyloxy)-2-methyl-propionyl chloride, 2-(ethoxycarbonyloxy)-2-methyl-propionyl chloride, 2-(methoxycarbonyloxy)-2-methyl-but-3-enoyl chloride, 2-(ethoxycarbonyloxy)-2-methyl-but-3-enoyl chloride, 2-(isopropoxycarbonyloxy)-2-methyl-but-3-enoyl chloride, 2-(n-butoxycarbonyloxy)-2-methyl-but-3-enoyl chloride, 2-(methoxycarbonyloxy)-2-methyl-but-3-enoyl bromide, 2-(methoxycarbonyloxy)-2-methyl-but-3-ynoyl chloride and 2-(ethoxycarbonyloxy)-2-methyl-but-3-ynoyl chloride.

The starting materials II are advantageously manufactured from α-hydroxyaldehyde-dialkyl acetals or glyoxal-dialkyl acetals, e.g. methylglyoxal-dimethyl acetal (German Pat. No. 1,252,193 and German Published Application DAS No. 2,338,665), which are converted, by means of Grignard compounds of alkynyl compounds, e.g. acetylene, using the method described in German Pat. No. 1,768,877, or by partial hydrogenation of the alkynyl compounds, as described in German Pat. No. 1,115,238, into the corresponding α-hydroxyaldehyde-dialkyl acetals. These α-hydroxyaldehyde-dialkyl acetals are converted, by reacting the hydroxyl group with chlorocarbonic acid esters, cleaving the acetal group and oxidizing the free aldehydes, to the corresponding acids, which are then phosgenated to give the starting material II.

The following amines are examples of suitable starting materials III: aniline, 2-, 3- and 4-chloroaniline, 2-, 3- and 4-methylaniline, 2-, 3- and 4-bromoaniline, 2-, 3- and 4-fluoroaniline, 2-, 3- and 4-methoxyaniline, 2,3-dichloroaniline, 3,4-dichloroaniline, 2,6-dichloroaniline, 3,5-dichloroaniline, 2,3,4-trichloroaniline, 3,4,5-trichloroaniline, 2,4,6-trichloroaniline and 2,3,6- and 2,3,5-trichloroaniline.

Where 3,5-dichloroaniline and 2-(methoxycarbonyloxy)-2-methyl-but-3-enoyl chloride are used as starting materials, the reaction can be represented by the following equations:

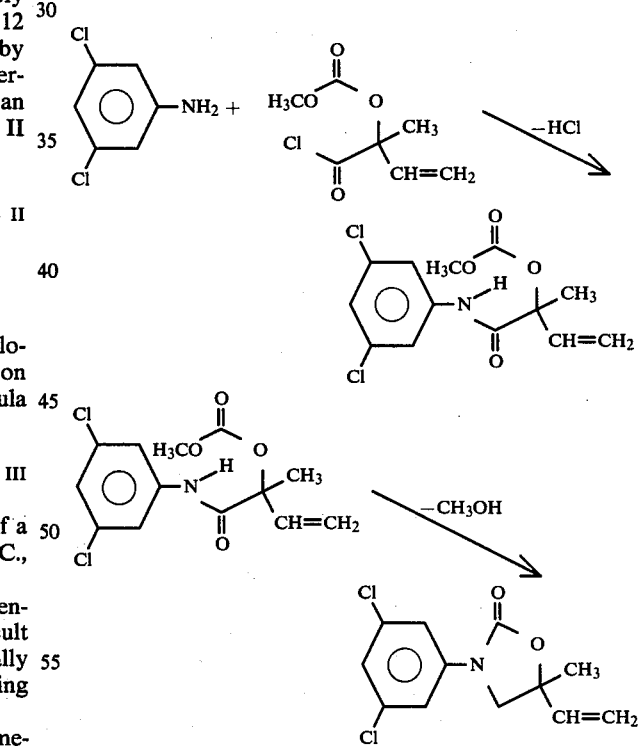

The reaction is as a rule carried out at from 0° to 150° C., preferably at from 20° to 120° C., under atmospheric or superatmospheric pressure.

The solvents used are, advantageously, solvents which are inert under the reaction conditions, Examples of suitable solvents are aromatic hydrocarbons, e.g. toluene, ethylbenzene, o-, m- and p-xylene and isopropylbenzene, halohydrocarbons, e.g. methylene chloride, chloroform, carbon tetrachloride, 1,1-dichloroethane, 1,2-dichloroethane, trichloroethane, tetrachloroethane, chlorobenzene, o-, m- and p-dichlorobenzene, and o-, m- and p-chlorotoluene, ethers, e.g. diisopropyl ether, di-n-butyl ether, cyclohexyl methyl ether, anisole, tetrahydrofuran and dioxane, and ketones, e.g. acetone, methyl ethyl ketone, diethyl ketone, methyl isopropyl ketone, diisopropyl ketone and cyclohexanone.

The hydrogen chloride liberated in the first stage of the reaction is neutralized by adding the stoichiometric amount of a base, preferably of a tertiary amine. Since the second stage of the reaction is base catalyzed, it is possible, when using a slight excess of tertiary amine, to obtain the desired end product in one step, without isolating the as yet not cyclized intermediate.

Examples of suitable bases are the following tertiary amines: trimethylamine, triethylamine, pyridine, dimethylaniline, quinoline, diethylaniline, N-ethylpiperidine, N-methylpyrrolidine, tri-n-propylamine, triisopropylamine, tri-n-butylamine, triisobutylamine, tri-sec.-butylamine, tri-n-pentylamine, tri-n-hexylamine, tri-n-heptylamine, tri-n-octylamine, tri-(2-ethylhexyl)-amine and tri-(2-methylpentyl)-amine.

The compounds obtainable by the process of the invention may be used as active ingredients in crop protection agents (German Laid-Open Application DOS No. 2,207,576).

In the Examples which follow, parts are by weight and bear the same relation to parts by volume as that of the kilogram to the liter.

EXAMPLE 1

(a) 1,1-dimethoxy-2-methyl-2-(methoxycarbonyloxy)-3-butene

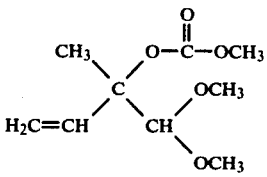

1,000 parts of toluene and 292 parts of 1,1-dimethoxy-2-methyl-2-hydroxy-3-butene are taken, 437 parts of a 30 percent strength solution of sodium methylate in methanol are then added slowly at from 90° to 100° C. and at the same time the methanol is distilled off, until the internal temperature reaches 107° C. 236 parts of methyl chlorocarbonate are subsequently added at 30° C. and stirring is continued for 8 hours. The mixture is then stirred with 500 parts of water, after which the organic phase is separated from the aqueous phase. Working up the organic phase by distillation gives, in addition to unconverted 1,1-dimethoxy-2-methyl-2-hydroxy-3-butene, 348 parts of 1,1-dimethoxy-2-methyl-2-(methoxycarbonyloxy)-3-butene, of boiling point/20 mm Hg = 107°-110° C. The yield is 85% of theory.

(b) 2-methoyl-2-(methoxycarbonyloxy)-but-3-enoyl chloride

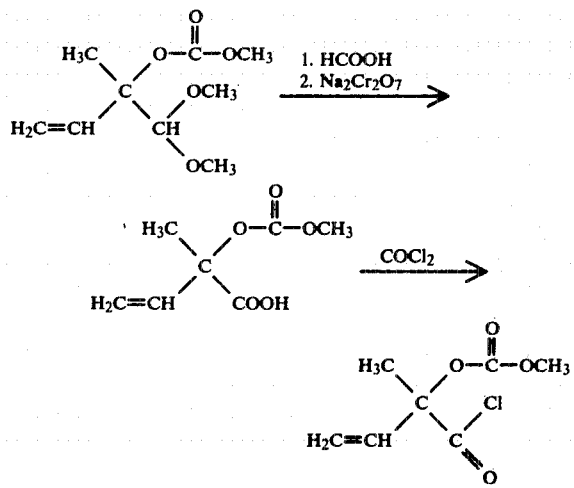

204 parts of 1,1-dimethoxy-2-methyl-2-(methoxycarbonyloxy)-3-butene and 102 parts of formic acid are heated at 70°-80° C. in a stirred apparatus fitted with a distillation unit. The methyl formate produced is distilled off at the same time. Volatile components are then distilled off under reduced pressure from a water pump, till the boiling point at 20 mm Hg reaches 30° C. The residue obtained consists of 151 parts of crude 2-methyl-2-(methoxycarbonyloxy)-but-3-en-1-al, which can be reacted further without additional purification. The yield is 95 percent.

(c) 143 parts of crude 2-methyl-2-(methoxycarbonyloxy)-but-3-en-1-al as obtained from the preceding stage are dissolved in 1,700 parts of acetone in a stirred apparatus. 156 parts of $Na_2Cr_2O_7 \times 2H_2O$, dissolved in 1,950 parts of 40 percent strength aqueous sulfuric acid, are added slowly at 15° C. whilst stirring, and stirring is then continued for one hour. The mixture is then extracted with three times 2,700 parts of methylene chloride. The combined methylene chloride extracts are free from the solvent under reduced pressure from a water pump. 145 parts (corresponding to a yield of 92%) of 2-methyl-2-(methoxycarbonyloxy)-but-3-enoic acid (O-methoxycarbonylvinyl-lactic acid), are obtained; this material can be used for the next step without purification.

(d) 145 parts of crude 2-methyl-2-(methoxycarbonyloxy)-but-3-enoic acid as obtained from the preceding stage are dissolved in 500 parts of toluene. 100 parts of phosgene are then passed into this solution at from 70° to 80° C. in the course of 3½ hours, whilst stirring. Working up the reaction product by distillation gives 138.5 parts of 2-methyl-2-(methoxycarbonyloxy)-but-3-enoyl chloride, boiling point/25 mm Hg = 105° C. The yield is 86.5% of theory.

(e) A solution of 24.9 parts of 2-methyl-2-(methoxycarbonyloxy)-but-3-enoyl chloride is added dropwise at room temperature (20° C.) to a mixture of 16.2 parts of 3,5-dichloroaniline and 11.1 parts of triethylamine dissolved in 100 parts of methylene chloride. During the addition, the temperature rises to 40° C. After completion of the addition, the mixture is stirred for 2 hours at 40° C. The reaction product is then washed with three times 50 parts of water, the organic phase is dried over sodium sulfate and the solvent is distilled off. A white crystalline precipitate remains, which is stirred with 100 parts of water. It is then filtered off and the filter residue is dried.

18.8 parts (65.7% of theory) of N-(3,5-dichlorophenyl)-5-methyl-5-vinyl-oxazolidine-2,4-dione, melting point 107° C., are obtained.

EXAMPLE 2

324 parts of 3,5-dichloroaniline and 300 parts of triethylamine are introduced into 1,600 parts of toluene in a stirred apparatus. 380 parts of 2-methyl-2-(methoxycarbonyloxy)-but-3-enoyl chloride are slowly added dropwise at 20° C. and the mixture is then heated for 6 hours at 110° C.

When it has cooled to room temperature, the mixture is washed with twice 400 parts of water. The organic phase is concentrated. The initially oily residue crystallizes on standing. After filtering off and drying the residue, 464 parts (82% of theory) of N-(3,5-dichlorophenyl)-5-methyl-5-vinyl-oxazolidine-2,4-dione, of melting point 107° C., are obtained.

We claim:

1. A process for the manufacture of a 2,4-dioxooxazolidine of the formula I

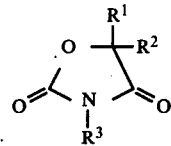

where $R^1$ and $R^2$ are identical or different and each is a saturated or a mono-olefinically unsaturated aliphatic hydrocarbon radical of 1 to 4 carbon atoms and $R^3$ is 3,5-dichlorophenyl, wherein an aniline compound of the formula III

where $R^3$ has the above meaning, is reacted with an α-hydroxycarboxylic acid derivative of the formula II

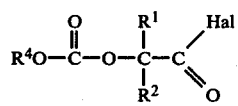

where $R^1$ and $R^2$ have the above meanings, Hal is halogen and $R^4$ is alkyl of 1 to 4 carbon atoms, in the presence of tertiary amine at 20° to 120° C.

2. A process as claimed in claim 1, wherein $R^1$ is methyl and $R^2$ is vinyl.

* * * * *